United States Patent
Schmitt et al.

(10) Patent No.: US 11,896,249 B2
(45) Date of Patent: Feb. 13, 2024

(54) LITHOTRIPSY SYSTEM HAVING A DRILL AND LATERAL EMITTER

(71) Applicant: GYRUS ACMI, INC., Westborough, MA (US)

(72) Inventors: Jeffrey M. Schmitt, Bolton, MA (US); Charles Baker, Rogers, MN (US)

(73) Assignee: Gyrus ACMI, Inc., Westborough, MA (US)

(*) Notice: Subject to any disclaimer, the term of this patent is extended or adjusted under 35 U.S.C. 154(b) by 112 days.

(21) Appl. No.: 17/356,733

(22) Filed: Jun. 24, 2021

(65) Prior Publication Data
US 2022/0000508 A1 Jan. 6, 2022

Related U.S. Application Data

(60) Provisional application No. 63/047,684, filed on Jul. 2, 2020.

(51) Int. Cl.
*A61B 17/22* (2006.01)
*A61B 18/26* (2006.01)
*A61B 17/00* (2006.01)

(52) U.S. Cl.
CPC .......... *A61B 17/2202* (2013.01); *A61B 17/22* (2013.01); *A61B 18/26* (2013.01); *A61B 2017/00402* (2013.01); *A61B 2017/22079* (2013.01); *A61B 2217/007* (2013.01); *A61B 2218/002* (2013.01); *A61B 2218/007* (2013.01)

(58) Field of Classification Search
CPC ................ A61B 17/22; A61B 17/2202; A61B 2017/22079; A61B 2217/007; A61B 2218/002; A61B 2218/007; A61B 18/26
See application file for complete search history.

(56) References Cited

U.S. PATENT DOCUMENTS

| 4,178,935 A | 12/1979 | Gekhman et al. |
| 5,944,687 A * | 8/1999 | Benett .................... A61B 18/26 606/15 |

(Continued)

FOREIGN PATENT DOCUMENTS

| CA | 2975886 A1 | 9/2016 |
| CN | 113876388 A | 1/2022 |

(Continued)

OTHER PUBLICATIONS

"European Application Serial No. 21182647.4, Extended European Search Report dated Nov. 22, 2021", 7 pgs.

(Continued)

*Primary Examiner* — Tuan V Nguyen
(74) *Attorney, Agent, or Firm* — Schwegman Lundberg & Woessner, P.A.

(57) ABSTRACT

A system to deliver energy to treat a mobile calculus, the system can include a drill and a lateral energy emitter. The drill can be configured to drill a recess into the mobile calculus or a passage through the mobile calculus. The lateral energy emitter can be configured to be advanced into the recess or the passage and to transmit the energy internal to the mobile calculus to fragment the mobile calculus. In some examples, the system can include a deployable capture portion to constrain a stone relative to the capture portion.

21 Claims, 7 Drawing Sheets

(56) References Cited

U.S. PATENT DOCUMENTS

| | | |
|---|---|---|
| 6,264,664 B1 * | 7/2001 | Avellanet ............. A61B 17/221 606/1 |
| 7,883,516 B2 | 2/2011 | Huang et al. |
| 8,414,656 B2 | 4/2013 | Davoudi et al. |
| 8,740,989 B2 | 6/2014 | Davoudi et al. |
| 8,753,351 B2 | 6/2014 | Huang et al. |
| 9,743,944 B1 | 8/2017 | Bonneau et al. |
| 9,949,615 B2 | 4/2018 | Zappia et al. |
| 9,968,403 B2 | 5/2018 | Hasenberg et al. |
| 10,067,304 B2 | 9/2018 | Yu et al. |
| 10,175,435 B2 | 1/2019 | Peng et al. |
| 10,188,411 B2 | 1/2019 | Bonneau et al. |
| 10,219,864 B2 | 3/2019 | Bonneau et al. |
| 10,258,485 B2 | 4/2019 | Davoudi et al. |
| 10,307,177 B2 | 6/2019 | Bonneau et al. |
| 10,321,923 B2 | 6/2019 | Degraaf et al. |
| 2005/0059981 A1 | 3/2005 | Poll |
| 2007/0208370 A1 * | 9/2007 | Hauser ............. A61B 17/22012 606/200 |
| 2008/0097251 A1 * | 4/2008 | Babaev ................. A61B 18/02 601/2 |
| 2015/0223828 A1 | 8/2015 | Desai et al. |
| 2016/0249942 A1 | 9/2016 | Olson |
| 2016/0256179 A1 | 9/2016 | Walish et al. |
| 2017/0119413 A1 | 5/2017 | Romo |
| 2018/0092693 A1 | 4/2018 | Falkenstein et al. |
| 2019/0113700 A1 | 4/2019 | Peng et al. |
| 2019/0159839 A1 | 5/2019 | Zhang et al. |

FOREIGN PATENT DOCUMENTS

| | | |
|---|---|---|
| WO | WO-2009074981 A1 | 6/2009 |
| WO | WO-2015163942 A1 | 10/2015 |

OTHER PUBLICATIONS

"European Application Serial No. 21182647.4, Response filed Sep. 6, 2022 to Extended European Search Report dated Nov. 22, 2021", 10 pgs.

"Intraluminal Crossing via Atherectormy (brochure)", Crosser CTO Recanalization Catheter, (2017), 10 pgs.

Antonelli, Jodi, et al., "(Abstract) A Novel Device to Prevent Stone Fragment Migration During Percutaneous Lithotripsy: Results From an In Vitro Kidney Model", J Endourol, (2016), 2 pgs.

* cited by examiner

LITHOTRIPSY SYSTEM HAVING A DRILL AND LATERAL EMITTER

CROSS-REFERENCE TO RELATED APPLICATION

This application claims the benefit of U.S. Provisional Patent Application Ser. No. 63/047,684 filed Jul. 2, 2020, the contents of which are incorporated herein by reference in their entirety.

TECHNICAL FIELD

The present disclosure relates to techniques for breaking obstructions, such as physiological calculi or "stones" using lithotripsy.

BACKGROUND

Medical endoscopes were first developed in the early 1800s and have been used to inspect inside the body. A typical endoscope consists of a distal end comprising an optical or electronic imaging system and a proximal end with controls for manipulating the tools and devices for viewing the image, with a solid or tubular elongate shaft connecting the ends. Some endoscopes allow a physician to pass tools or treatments down a hollow working channel, for example, to resect tissue or retrieve objects.

Over the past several decades, several advances have been made in the field of endoscopy, and in particular relating to the breaking up of physiologic calculi in the bile ducts, urinary tract, kidneys, and gall bladder. Physiological calculi in these regions may block ducts and cause a patient a substantial amount of pain and therefore must be broken down and/or removed. Different techniques have been developed to break up stones, including ultrasonic lithotripsy, pneumatic lithotripsy, electro-hydraulic lithotripsy (EHL), and laser lithotripsy including dissolution of calculi using green light, YAG, or holmium lasers.

Overview

The present inventor has recognized, among other things, that problems to be solved in performing laser lithotripsy in a living being include a surgeon being able to easily capture, fragment and remove the fragments of a stone located within the body. The present subject matter can provide solutions to these problems and other problems.

In an example, a system to deliver energy to treat a stone, such as a mobile calculus located inside a living being can include a drill configured to drill a recess into the mobile calculus or a passage through the mobile calculus. The system can further include a transducer configured to be advanced into the recess or passage and to transmit the energy internal to the mobile calculus to fragment the mobile calculus. In some examples, the drill can be located at a distal end portion of a delivery member having an elongate shaft that is deliverable to a treatment site through a working channel with the transducer located proximal of the drill. In some examples, the system further includes a capture portion configured to constrain movement of at least a portion of the mobile calculus relative to the capture portion.

In another example, a method to treat a mobile calculus in a patient can include drilling a hole through the mobile calculus to create a recess into the mobile calculus or a passage through the mobile calculus to receive a delivery member having an acoustic transducer. The method can further include advancing the acoustic transducer into the passage, and exciting the acoustic transducer to transmit acoustic energy to the mobile calculus to fragment the mobile calculus.

In another example, a method of controlling a lithotripter can include providing a lithotripsy system including a drill located at a distal end portion, an acoustic transducer located proximal of the drill, and a capture portion. The method can further include issuing or receiving a first control signal to actuate the drill; issuing or receiving an input to deploy the capture portion; and issuing or receiving a second control signal to excite the acoustic transducer.

Benefits of the approaches described herein include reduced time to perform a percutaneous nephrolithotomy.

This overview is intended to provide an overview of subject matter of the present patent application. It is not intended to provide an exclusive or exhaustive explanation of the invention. The detailed description is included to provide further information about the present patent application.

Figure 1:
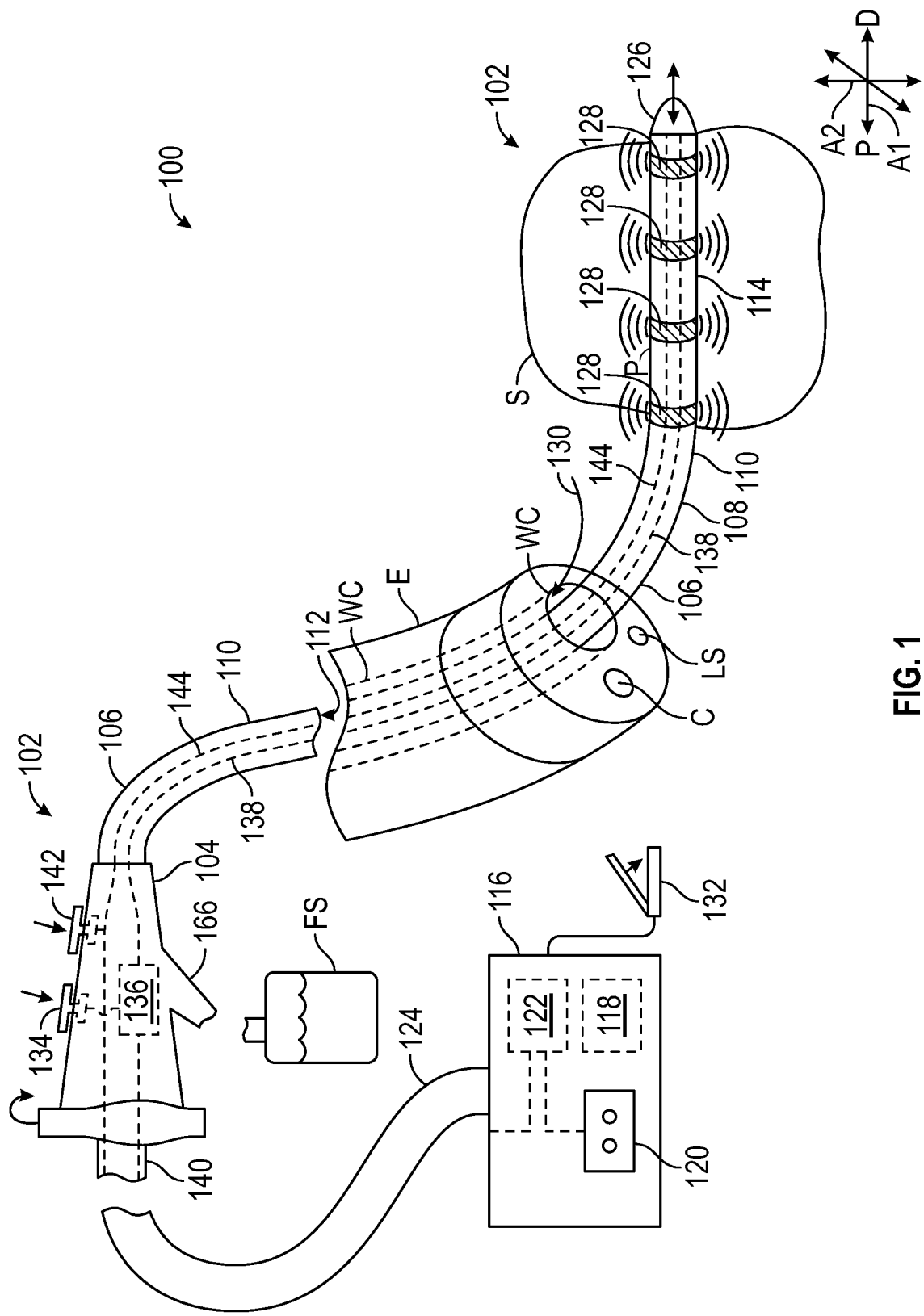
FIG. 1 illustrates an isometric view of a portion of a lithotripsy system, in accordance with at least one example.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure provides examples of systems and methods that can help address the problem of fragmenting and collecting stones during lithotripsy, such as ultrasonic lithotripsy, but aspects described herein may be used with other types of lithotripsy.

In ultrasonic and other acoustic lithotripsy, the practitioner can break a stone into smaller fragments by applying a sound wave to the stone. For example, a lithotripsy probe can deliver an oscillating pulse of ultrasonic energy with variable amplitudes and/or frequencies to the stone. Once the stones have been broken into relatively small fragments, the practitioner can extract the small fragments through the endoscope.

Fragmenting and collecting stones can be challenging because the stones can be free-floating, mobile calculi, so they may move during the process of fragmenting. In addition, the physical characteristics of the stone, such as hardness can vary throughout different portions of the stone. For example, the outer portion of the stone can often be harder than an inner portion of the stone. Stones can be present in various organs of the body, including, but not limited to kidney, bladder, ureter, bile ducts and gallbladder.

Benefits of the approaches described herein include, among other things, reducing the time it takes to fragment and remove stones by capturing the stone for treatment, communicating energy to the stone from within the stone to target the generally softer inner part of the stone, and maintaining capture of at least a portion of the fragmented stone for removal. These approaches can lead to shorter procedure times because the position of the stone is controlled and known during the lithotripsy process, reducing retropulsion and other unwanted movement of the stone which can lead to a surgeon having to "chase" the stone throughout the procedure. Maintaining capture of the stone fragments can also improve the post-procedure stone free rate in a patient.

For the purposes of this disclosure, "proximal" refers to an end of the system that is closer the device operator during use, and "distal" refers to an end of the system that is distal, or further from the device operator during use.

FIG. 1 illustrates an isometric view of an example of a lithotripsy system 100 including a lithotripter 102 having a housing 104, such as a handle. The lithotripter 102 can include a delivery member 106 that is deliverable to a treatment site through a working channel WC of an endoscope E. The endoscope E can also include a light source LS and a camera C.

The delivery member 106 can include a flexible or a rigid elongate shaft 108 having a tubular structure. Suitable materials for the delivery member include, but are not limited to, polytetrafluoroethylene ("PTFE"), polyethylenes ("PE") and polyamides. The elongate shaft 108 can include an outer surface 110 and at least one lumen 112 extending therethrough, the lumen being suitable for passage of components and materials that communicate with end effectors described herein.

The delivery member 106 can include an end effector such as a probe 114 at a distal end that is deliverable to a treatment site. The probe 114 can be configured to deliver energy to fragment a mobile calculus such as a stone located in a bile duct, urinary tract, kidney or gall bladder. The probe 114 of the lithotripter 102 can be introduced into a patient, driven by the delivery member 106 through a working channel WC of an endoscope E or similar instrument. The probe 114 can be flexible or rigid.

The lithotripter can be connected to a generator 116 (e.g., a signal generator, an energy generator). The generator 116 can include a power source 118 or can be couplable to an external power source. The generator 116 can also include an input 120 to receive an instruction from an operator, and may include a controller 122 having processing circuitry for determining actions based on operator input and for sending control signals via an output 124 for communication to the lithotripter 102. The generator 116 can produce signals and send them to the lithotripter 102 probe 114 to cause the probe 114 to emit acoustic energy. Acoustic energy can include sound waves, sonic waves, ultrasonic waves or shock waves, or any combination of these. Acoustic energy can be delivered to a stone S to deteriorate, crack and thereby fracture the stone S. The examples herein are described with reference to ultrasonic applications but any suitable acoustic energy for fracturing stones can be provided. The terms sonic and ultrasonic may be used herein interchangeably, and can include an suitable acoustic energy for fragmenting stones.

Features of the probe 114 can provide improved fragmenting of the stone S. For example, the probe 114 can include a drill 126 (which need not include a rotating drill bit), such as an ultrasonic drill that emits acoustic energy, in a longitudinal direction A1, to drill a hole in the stone. The probe 114 can also include one or more lateral emitters 128 such as a lateral ultrasonic transducer to deliver acoustic energy inside the hole to fragment the stone from the inside out.

The drill 126 can be coupled to the elongate shaft 108 and can be located at a distal tip of the probe 114. The drill 126 can include at least a portion that extends distal of the elongate shaft 108. In the example of FIG. 1, the drill 126 can be configured to emit ultrasonic energy in the longitudinal direction A1. The drill 126 can cause mechanical modification or destruction of the stone S by producing pulsatile shock waves that move generally along the longitudinal direction A1. The drill 126 can be configured to drill a hole, such as a recess into, or a passage P through, the stone S. FIG. 1 shows an example including a drill 126 that has drilled a passage P through the stone S.

The drill 126 can be an ultrasonic emitter that receives ultrasonic energy from a remotely located ultrasonic transducer 136, which will be referred to as a drill transducer 136 for the purposes of clarity over other emitters and transducers in this disclosure. The drill transducer 136 can be located, for example, in the housing 104 of the lithotripter 102. The drill transducer 136 can transmit ultrasonic energy in a generally longitudinal direction A1, distally out of the housing 104. Ultrasonic energy can be transmitted from the drill transducer 136 to the drill 126 via an ultrasound transmission member 138. The ultrasound transmission member 138 can be coupled to the drill transducer 136 at a proximal end and to the drill 126 at the distal end. The ultrasound transmission member 138 can be formed of any material that is capable of transmitting the ultrasound energy from the drill transducer 136 to the drill 126, including but not limited to metal, metal alloys, shape memory alloys, polymers, ceramics, fibers, crystals or composites thereof.

The drill transducer 136 can be electrically couplable to the generator 116, such as by a connector 140, to receive signals for operating the drill 126. The drill transducer 136 can be actuated by, for example, an operator depressing a foot pedal 132 that is in electrical communication with the generator 116, or can be actuated by a drill actuator 134 coupled to the housing 104 that is in electrical communication with the generator 116. Any other suitable actuator for controlling activation of the drill 126 may be provided.

Although the drill 126 is described as an ultrasonic drill, in some examples, other types of drills may be provided, including but not limited to, a rotational drill operated by a motor. Like the drill transducer in the example of FIG. 1, the motor can be located remotely of the probe 114, such as in the housing 104, and the motor can be coupled to the drill 126 via a rotational transmission member. In other words, in a variation on the example of FIG. 1, a rotational motor can be provided in place of the drill transducer 136, and a rotational transmission member can be provided in place of the ultrasound transmission member 138.

In addition to using an ultrasonic emitter for drilling, the probe 114 can include at least one radial or lateral emitter 128, such as a lateral ultrasonic emitter configured to direct ultrasonic energy in a radial or lateral direction A2, outward and away from the longitudinal direction A1 such as toward an internal surface (passage P) of the stone S. In the example of FIG. 1, the at least one lateral emitter 128 includes a plurality or array of lateral emitters 128.

Each of the lateral emitters 128 can direct ultrasonic energy in the lateral direction A2, with each of the lateral emitters 128 located along a different longitudinal position on the probe 114. In some examples the lateral emitters 128 can be spaced apart along the longitudinal direction A1. The lateral emitters 128 can extend laterally or radially around the probe 114. In some examples, the lateral emitters 128 can extend around the entire 360 degree circumference of the probe 114, or around a perimeter of the probe 114 when a probe has a non-circular cross-section in direction lateral or perpendicular A1 to the longitudinal direction A1. In other examples, the lateral emitters 128 may only partially wrap around the probe 114.

The lateral emitters 128 can be located proximal of the drill 126. A benefit of this arrangement is that the lateral emitter 128 can follow the drill 126 so that after the drill 126 prepares the passage P in the stone S, the lateral sonic emitter 128 can be advanced through the passage P. When activated, such as by lateral emitter actuator 142 that is in electrical communication with the lateral emitters 128 via electrical element 144 such as a wire, the lateral emitters 128 can be configured to emit ultrasonic energy into to the passage P and internal to the stone S to fracture the stone S from the inside of the stone S.

Similar to the drill transducer 136, the lateral emitter 128 can include an ultrasonic or other acoustic transducer. An electrical-to-acoustic transducer is a component that can convert an electrical signal into variations in a physical quantity such as sound waves or pressure. Ultrasonic transducers can include linear piezo electric stacks having piezoelectric elements located between two metal plates. Such piezo electric elements can convert electrical energy (e.g., electric current) into mechanical energy (e.g., sound waves, sonic waves, ultrasonic waves, shock waves). Piezoelectric elements can include crystal, such as quartz, having physical characteristics that results in the crystal undergoing mechanical stress when subjected to an electric field that causes the crystal to change size or shape. The piezoelectric elements alternatively expand and contract in response to an alternating electric field, such as can be supplied by the generator 116. This expansion and contraction can generate sound waves that can be delivered to a stone S to fracture the stone S. In some examples, an optoacoustic transducer, or magnetoresistive stacks can be provided to convert optical energy received from a generator (e.g., optical energy generator in place of generator 116) into acoustic energy.

To help locate a stone S relatively stationary relative to the working channel WC of the endoscope E while drilling the hole, and relatively stationary to the probe 114 (except for the probe's longitudinal A1 movement through the stone), suction, as denoted by suction arrow 130, can be applied through the working channel WC. The suction 130 can cause the stone S to be "captured" by pulling the stone S towards the working channel WC and thus pulling the stone S towards the drill 126 of the probe 114 for drilling.

Figure 3:
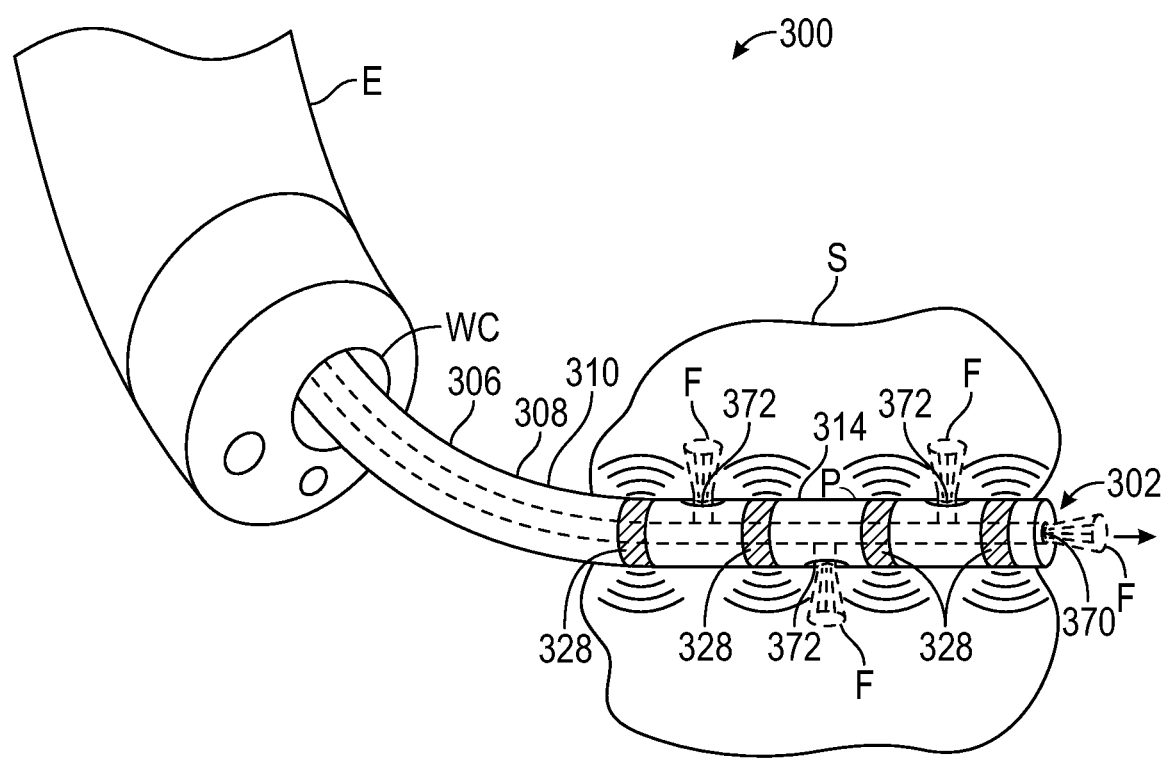
FIG. 3 illustrates an isometric view of a portion of a third lithotripsy system, in accordance with at least one example.

Some lithotripsy systems described herein can include a fluid input 166 for receiving fluid from a fluid storage FS and delivering fluid to a treatment site, as described in the illustrative example of FIG. 3.

While the illustrative examples of this disclosure are generally described with reference to lithotripsy devices including acoustic, ultrasonic and fluid emitters (e.g., jets emitting kinetic energy via a moving fluid), other forms of energy, such as lasers can be provided as the drill 126 and/or lateral emitters 128 described herein. For example, the drill 126 or the at least one lateral emitter 128 can emit laser energy instead of, or in addition to acoustic or ultrasonic energy. In such an illustrative example, the lithotripsy system can receive laser energy from a laser generator (e.g., in place of the signal generator 116). In such an example, at least one of the drill 126 and the lateral emitter 128 can be laser emitters that receive laser energy via at least one laser fiber (e.g., in place of ultrasound transmission member 138). In other words, the drill can be configured to emit laser energy to drill a passage through the stone S and the at least one lateral emitter can be configured to emit laser energy into the passage P to fragment the stone S. The laser energy being received from a laser generator and transmitted to the drill and the lateral emitter via a laser fiber. In some examples, such a lateral emitter can include an outcoupler or a side firing laser to direct the laser energy laterally.

Figure 2:
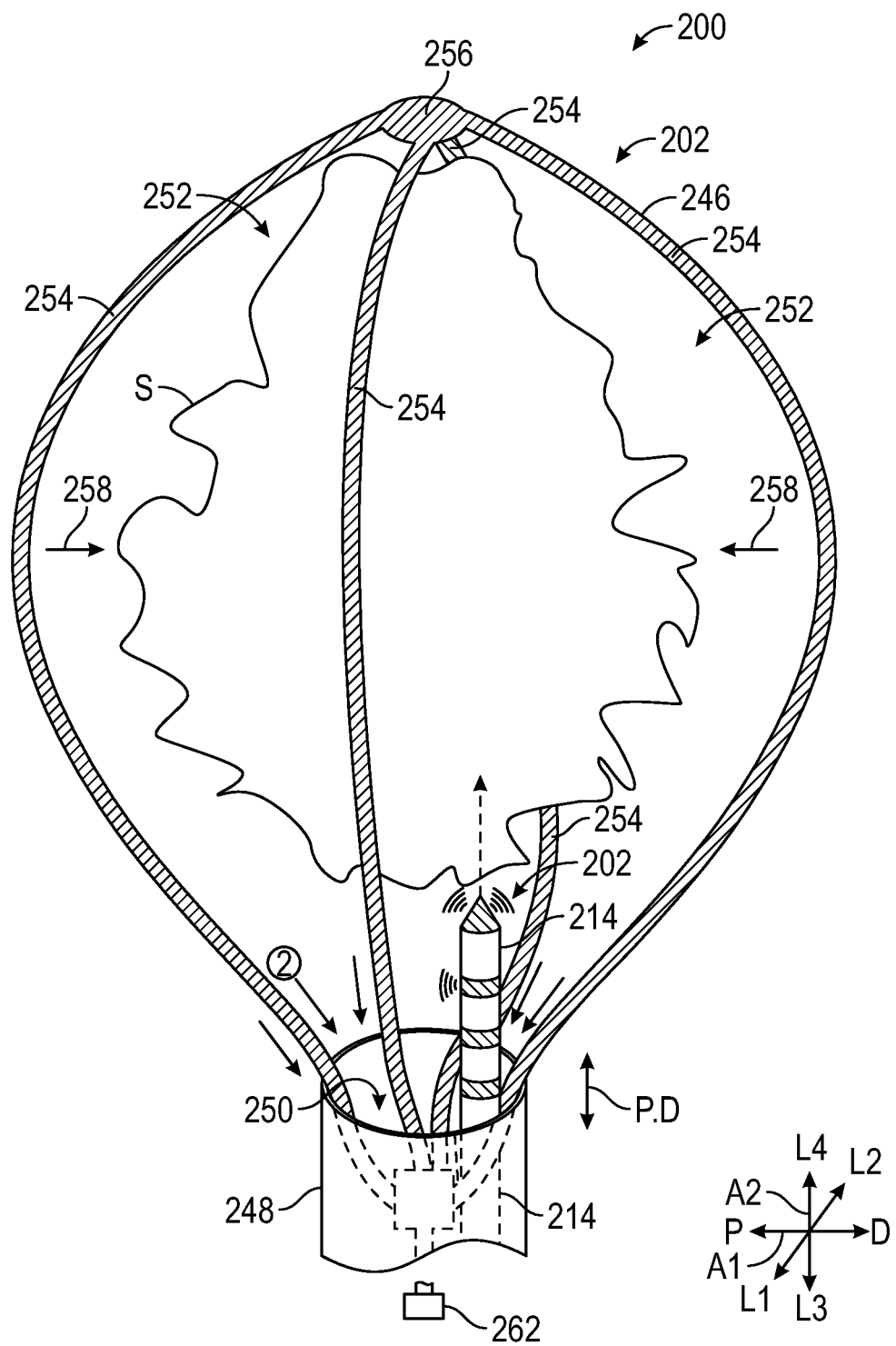
FIG. 2 illustrates an isometric view of a portion of a second lithotripsy system, in accordance with at least one example.

FIG. 2 illustrates an isometric view of a portion of a second lithotripsy system 200 including a lithotripter 202. The lithotripsy system 200 can include the features of the lithotripsy system 100 of FIG. 1. Like numbers can represent like elements, therefore for the sake of brevity, all aspects of the lithotripsy system 200 may not be described in further detail.

The lithotripsy system 200 can include all the features of the lithotripsy system 100 of FIG. 1. For example, a lithotripter 202 and a probe 214 can be the same or similar to the lithotripter 102 and probe 114. The lithotripsy system 200 can also include a capture portion 246 (e.g. a capture structure). The capture portion 246 can capture a stone S and hold it while the probe 214 drills a hole, such as a recess or passage into the stone (passage shown in FIG. 1). The capture portion 246 can constrain movement of at least a portion of the stone S relative to the capture portion 246. The capture portion 246 provides a benefit similar to or in addition to the suction (suction arrow 130, FIG. 1) that can be applied to the stone S via the working channel as shown and described in the lithotripsy system 100 of FIG. 1. The capture portion 246 holding the stone can make it easier for the probe 214 to drill through the stone S and prevent a surgeon from having to "chase" a moving stone S. Capturing stone fragments more efficiently can reduce procedure time.

In the lithotripsy system 200, the capture portion 246 can be deployed distally from the working channel WC or another channel of the endoscope E (FIG. 1). The capture portion 246 can hold the stone S and constrain the stone relative to the capture portion 246, and thereby constrain the stone S relative to the probe 214 while drilling the hole (except for the probe's longitudinal movement through the stone S).

In some examples, the capture portion 246 can be retracted at least partially into a sheath 248 of the lithotripter 202 or into the working channel WC to pull the stone S towards the working channel WC and the probe 214. While the capture portion 246 may not eliminate all movement of the stone S, movement of the stone S, especially movement of the stone S away from the probe 214 is reduced.

The sheath 248 can guide the probe 214 and the capture portion 246 through the working channel. The capture portion 246 can serve as a stone S retention member configured to be movable from a stored state housed within a lumen 250 of the sheath 248 to a deployed state to capture a stone S. The sheath 248 can have any suitable cross section, including but not limited to: circular, oval, elliptical, polygonal or irregular.

In FIG. 2, the capture portion 246 is shown in the deployed state and the direction of movement from the stored state to the deployed state and vice-versa is shown by movement arrow P-D. A deployed state can refer to a state in which the capture portion 246 is advanced distal of the sheath 248 (e.g., expanded) such as by a capture actuator 262 located on a housing (e.g., 104, FIG. 1). Movement from the stored state to a deployed state can include movement of the capture portion 246 distal along a longitudinal direction A1, as well as expansion in a lateral direction A2, such as but not limited to lateral directions L1, L2, L3, L4. In other words, deployment can include the capture portion 246 being movable in a direction having a longitudinal component along the proximal-distal direction and a lateral component relative to the elongate shaft when actuated by an operator.

The capture portion 246 can include at least one receiving opening 252 to receive a stone S into a receiving cavity 260. The capture portion 246 can include at least one strut 254 to capture the stone S. FIG. 2 includes four deformable struts 254 separating four receiving openings 252, but any suitable number of struts 254 and receiving openings 252 to permit entry of a stone S into a capture portion 246 and capture of the stone S by the struts may be provided.

In some examples the struts 254 can form a basket or scaffold. The struts 254 can converge at a distal end. The struts 254 can be formed as four individual struts 254 that are joined together at a distal end coupling such as a hub 256, or the struts 254 may be integrally formed with one another or overlap with one another. Suitable materials for the struts 254 can include resilient and biocompatible materials such as nitinol, spring stainless steel, shape memory polymer, any other suitable shape-memory material, and including alloys and combinations of such materials.

In some examples, retracting the capture portion 246 proximally can cause the struts 254 to move proximally and at least partially into the lumen 250 of the sheath 248. This proximal movement can cause the proximal portion of the struts 254 to be compressed and deflected at least partially inward (as shown by deflection arrows 258), thereby narrowing or reducing the volume of the receiving cavity 260 so that the capture portion 246 can close in on, and in some cases press onto the stone S to limit movement of the stone S. The capture portion 246 can be used with any of the lithotripsy systems 100, 200, 300, 400 and 500 described herein.

FIG. 3 illustrates an isometric view of a portion of a third lithotripsy system, in accordance with at least one example. The lithotripsy system 300 of FIG. 3 can include features of the lithotripsy systems 100, 200 of FIGS. 1 and 2. Like numbers can represent like elements, therefore for the sake of brevity, all aspects of the lithotripsy system 300 may not be described in further detail.

The lithotripsy system 300 can include all the features of the lithotripsy system 100 of FIG. 1. For example, the lithotripter 302 can include features of the probe 114 including the lateral sonic emitters 128 of the lithotripter 102 as probe 314 and lateral emitters 328. The lithotripter 302 can also include a delivery member 306 having an elongate shaft 308 including a tubular structure having an outer surface 310. The lateral emitters 328 can deliver ultrasonic energy to the stone S to fragment the stone S as described in FIG. 1. The delivery member 306 can be delivered to a treatment site via a working channel WC of an endoscope E.

In addition to the features of the lithotripsy system 100 of FIG. 1, the delivery member 306 can include a fluid delivery channel 364 extending therethrough. The fluid delivery channel 364 can be configured to receive fluid from a fluid storage (FS; FIG. 1) via a fluid input (166; FIG. 1).

The fluid delivery channel 364 can be in fluid communication with at least one fluid port 270, 272 through the outer surface 310 of the elongate shaft 308. The fluid delivery channel 364 can deliver the fluid F to at least one fluid port 370, 372, such as a jet or nozzle configured to dispense the fluid F outward from the surface 310 of the probe 314. The fluid port 370, 372 can be configured to cause the fluid F to exit the probe under pressure.

As shown in FIG. 3, instead of an ultrasonic drill, the drill 326 can be provided in the form of a distal fluid port 370 located at a distal tip of the probe 314. The distal fluid port 370 (e.g., drill, fluid drill) can be in fluid communication with the fluid delivery channel 364 to receive the fluid and dispense the fluid to the treatment site under pressure. Fluid exiting the distal fluid port 370 can be configured to deteriorate the stone S to drill a hole, passage or recess in the stone S.

The fluid delivery channel 364 (or a second fluid delivery channel) can also deliver fluid to at least one lateral fluid port 372. Fluid exiting the lateral fluid port 372 can aid in deteriorating the stone S and providing cooling fluid to the area proximate the stone S. The lateral fluid port 372 can include a jet or nozzle configured to deliver fluid under pressure laterally outward from the probe 314 to cause fractures or microfractures in the stone S. The lateral fluid ports 372 can be longitudinally and/or laterally (e.g., can be radially or another lateral direction) spaced apart along the probe 314. Benefits of delivering fluid to the stone S as described include shorter procedure time and reduction of localized fluid temperature. Suitable fluids for delivery to the stone S to fracture the stone S can include, but is not limited to, an aqueous solution such as saline.

The combination of the application of ultrasonic energy and pressurized fluid to fracture a stone S can expedite fracture of the stone S and keep the treatment site cooler. The lithotripsy system 300 of FIG. 3 can be combined with the capture portion 246 of FIG. 2, to capture and further expedite removal of stone fragments.

Figure 4A:
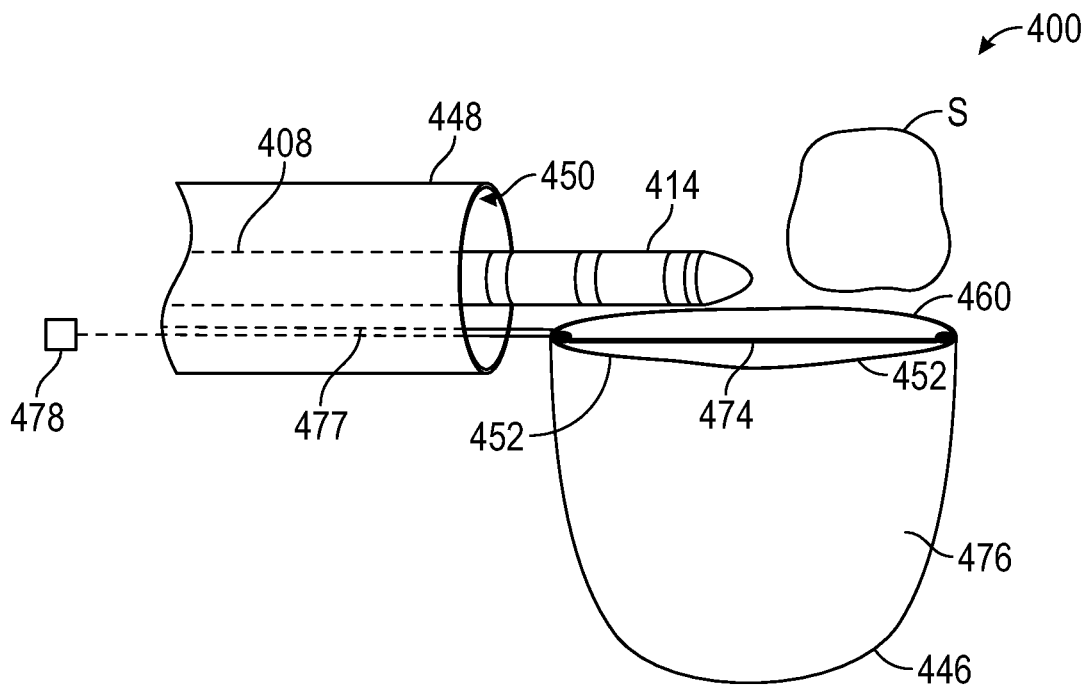
FIG. 4A illustrates a side view of a portion of a fourth lithotripsy system in a stored state, in accordance with at least one example.
Figure 4B:
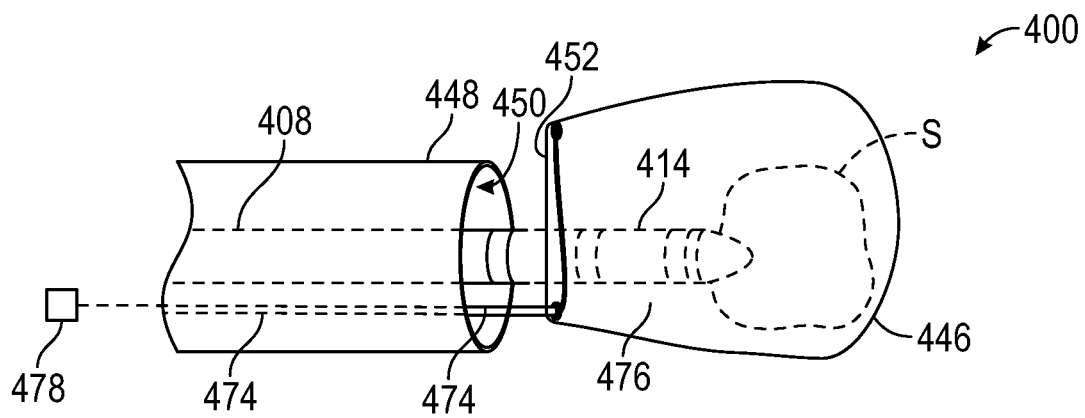
FIG. 4B illustrates a side view of a portion of the fourth lithotripsy system in a deployed state.

FIG. 4A illustrates a side view of a portion of a fourth lithotripsy system 400 in a stored state. FIG. 4B illustrates a side view of a portion of the fourth lithotripsy system 400 in a deployed state. The lithotripsy system 400 of FIGS. 4A and 4B can include features of the lithotripsy systems 100, 200 and 300 of FIGS. 1, 2 and 3. Like numbers can represent like elements, therefore for the sake of brevity, all aspects of the lithotripsy system 400 may not be described in further detail.

The lithotripsy system 400 can include a delivery member 408 including aspects of any of the delivery members 106, 206, 306 and a probe 414 including aspects of any of the probes 114, 214, 314 described herein, shown and described with respect to FIG. 1, 2 or 3. The lithotripsy system 400 can also include a capture portion 446 deployable from a lumen 450 of a sheath 448 and can include some aspects of the capture portion 246 of FIG. 2.

The capture portion 446 can include aspects of the capture portion 246. The capture portion 446 can include a layer 476 that defines a receiving cavity 460. The receiving cavity 460 can be accessible to receive a stone S through a receiving opening 452. A closure member 474 can be actuated by a capture actuator 462 to reduce the opening 452. The layer 476 can be made of a compliant material such as a mesh. The layer 476 can include, but is not limited to, the type of meshes that are used in hernia and other tissue repair procedures. In some examples, the layer 476 may be at least partially see-through such that visibility during a procedure is improved. In some examples, the layer 476 may be formed of a thin sheet of pliable, flexible polymeric material such as a film. To improve visibility the film may be a transparent film.

The capture portion 446 can be deployable from a compressed state when positioned in the sheath 448 to the receiving state when deployed distally from the sheath 448 as shown in FIGS. 4A and 4B. In the receiving state (FIG. 4A) the capture portion 446 can be configured to receive a stone S into the opening (e.g., receiving opening). When the closure member 474 is actuated, the receiving opening 452 can deform and reduce to enable the capture portion 446 to constrain the stone S in the capture state (FIG. 4B).

In some examples, the stone S can be captured by being scooped into the receiving opening 452. For example, when an operator manipulates a closure actuator 478, a closure member 474 can move the capture portion 446 in one or more of a scooping, pivoting or closing motion. When a stone S to be captured passes through the receiving opening 452 and into the receiving cavity 460, an operator can actuate, such as by sliding the closure actuator 278, to cause movement of the closure member 474 which causes a scooping, pivoting or closing action of the capture portion 446 to occur. In addition to scooping, the opening can be reduced from an open size to a less-open or closed size. The closure actuator 478 be a sliding or pivoting actuator on a housing of the lithotripter, but may be any other suitable actuator that can cause the closure member 474 to perform a scooping, pivoting and/or closing motion of the capture portion 446.

Figure 5A:
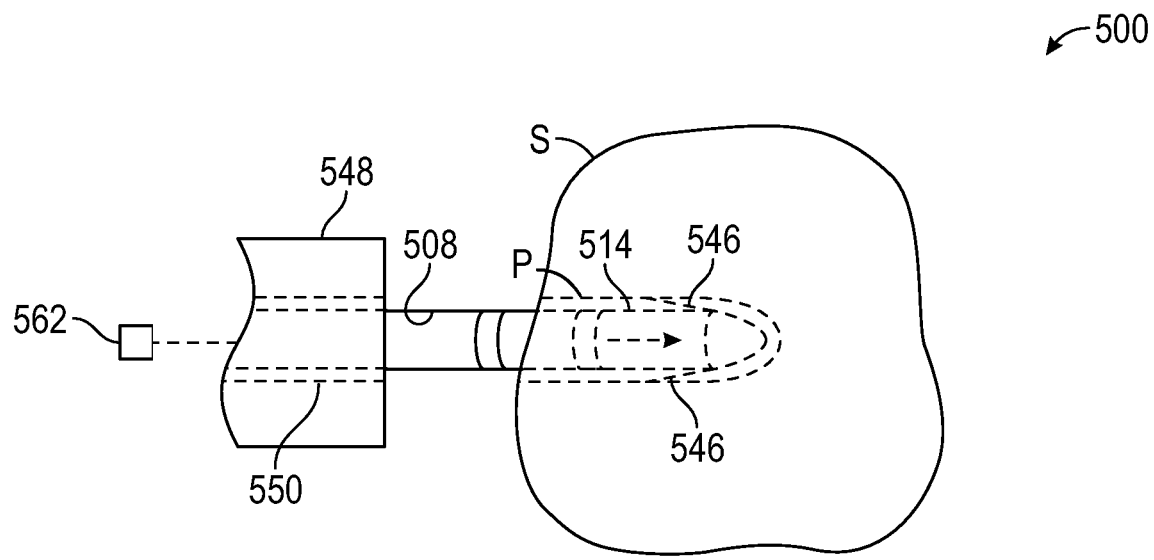
FIG. 5A illustrates an isometric view of a portion of a fifth lithotripsy system in a first deployed state for receiving a stone, in accordance with at least one example.
Figure 5B:
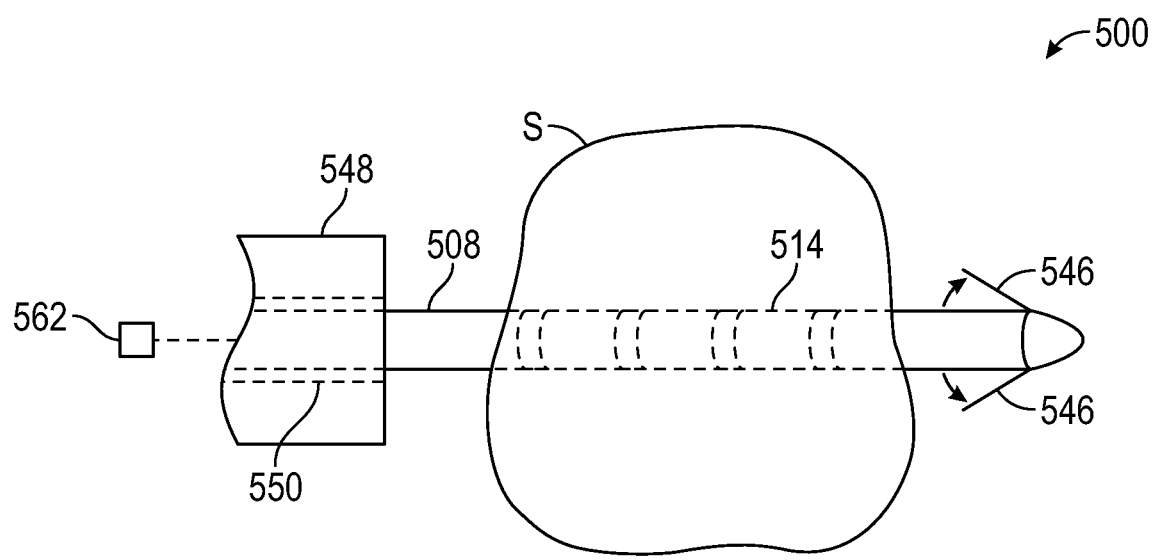
FIG. 5B illustrates an isometric view of a portion of the fifth lithotripsy system in a second deployed state for capturing a stone, in accordance with at least one example.

FIG. 5A illustrates an isometric view of a portion of a fifth lithotripsy system 500 in a first deployed state for receiving a stone S. FIG. 5B illustrates an isometric view of a portion of the fifth lithotripsy system 500 in a second deployed state for capturing a stone S.

The lithotripsy system 500 of FIGS. 5A and 5B can include features of the lithotripsy systems 100, 200, 300 and 400 of FIGS. 1, 2, 3 and 4. Like numbers can represent like elements, therefore for the sake of brevity, all aspects of the lithotripsy system 500 may not be described in further detail. FIGS. 5A and 5B are described together.

The lithotripsy system 500 can include a delivery member 508 including aspects of any of the delivery members 106, 206, 306, 406 and a probe 514 including aspects of any of the probes 114, 214, 314, 414 described herein, shown and described with respect to FIGS. 1, 2, 3 and 4. The lithotripsy system 500 can also include a capture portion 546 deployable from a lumen 550 of a sheath 548 and can include some aspects of the capture portions 246 and 446 of FIGS. 2 and 4.

The lithotripsy system 500 can include a capture portion 546 that can be maintained in an undeployed state (e.g., a compressed state), during delivery through a working channel (WC, FIG. 1) to a stone treatment site, such as a kidney. A stone S can be drawn towards the working channel during drilling, for example, by the suction (e.g., suction arrow 130) described with respect to the example of FIG. 1. The suction can be applied to the stone S via an opening at the distal end of the working channel (WC; FIG. 1)

The capture portion 546 can remain in an undeployed state as the probe 514 drills through the stone S. The capture portion 546 can be configured to be advanced through the passage and to be deployed distal of the stone S. As the probe exits the distal side of the stone S, the capture portion 546 can be deployed automatically, for example by a spring-loaded connection between the probe 514 and the capture portion 546, or by an operator actuating a capture actuator 562 that is operably coupled to the capture portion 546. The capture actuator 562 can be a sliding actuator, or a pivoting lever actuator on the housing (e.g., 104; FIG. 1), however any suitable actuator can be provided. The capture portion 546 can be configured to constrain movement of at least a portion of the stone S relative to the capture portion 546 so that at least one of drilling, fragmenting or collecting can be facilitated more easily.

Figure 6:
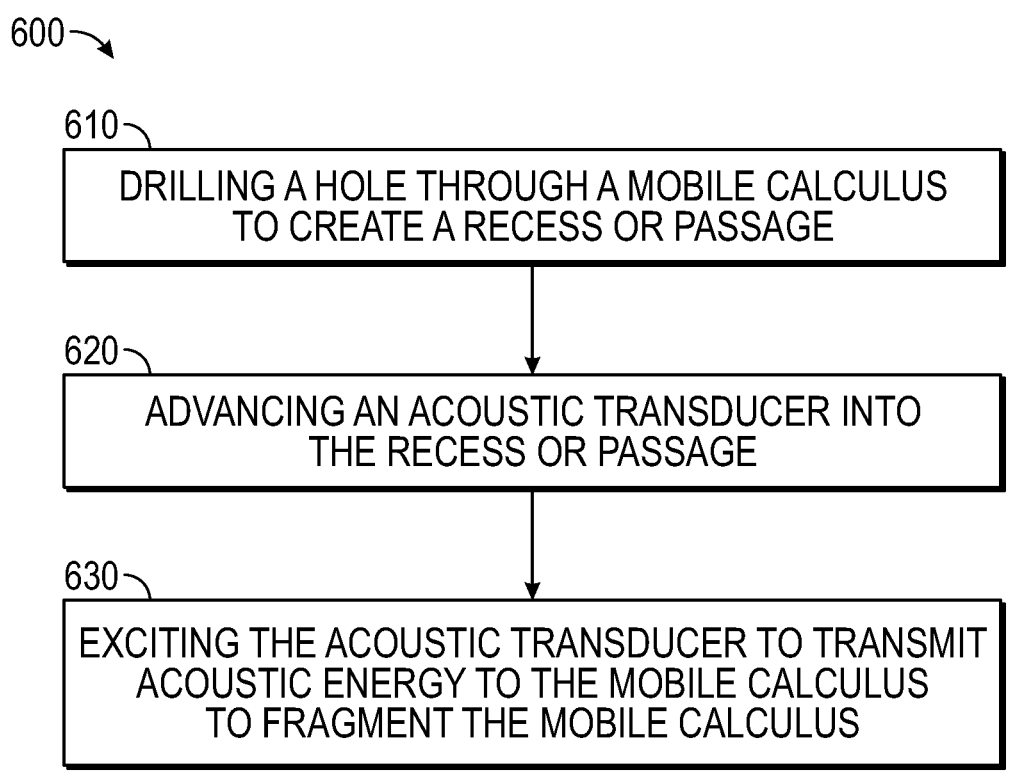
FIG. 6 illustrates a flow chart of a method to treat a mobile calculus in a patient.

FIG. 6 is a flow chart illustrating a method 600 to treat a mobile calculus such as a stone in a kidney, bladder, ureter or gallbladder. The method 600 can be performed using any of the lithotripsy systems 100, 200, 300, 400 and 500 of FIG. 1-3, 4A, 4B, 5A and 5B can be used with the method 600, but the method 600 can also be used with other lithotripsy systems. Likewise, the lithotripsy systems 100, 200, 300, 400 and 500 of FIGS. 1-3, 4A, 4B, 5A and 5B. can be used with other methods. In some examples, steps of the method 600 can be omitted or added.

Step 610 can include drilling a hole in a stone to create a recess into the stone or a passage through the stone to receive a delivery member having an acoustic transducer, such as a lateral sonic emitter.

Step 620 can include advancing the acoustic transducer into the recess or passage.

Step 630 can include exciting the acoustic transducer to transmit acoustic energy to the stone to fragment the stone.

In some examples, prior to performing step 610, the method 600 can further include suctioning a stone to draw the stone towards a working channel of an endoscope and/or deploying a capture portion configured to receive and constrain at least a portion of the stone; receiving the stone into the opening to capture the stone; and constraining movement of the stone relative to the acoustic transducer while exciting the acoustic transducer.

In some examples, step 630 can also include providing fluid through the delivery member having a tubular structure including an outer surface and a fluid delivery channel extending therethrough, the fluid delivery channel in fluid communication with a fluid port in the outer surface, wherein providing the fluid causes fluid to be dispensed from the fluid port into the recess or the passage to cause deterioration of the stone.

In some examples, after performing step 630, the method can further include capturing at least a portion of the fragmented stone and removing the stone from the patient and/or suction a region around at least a portion of the fragmented stone to move at least a portion of the fragmented stone into the working channel of an endoscope.

Figure 7:
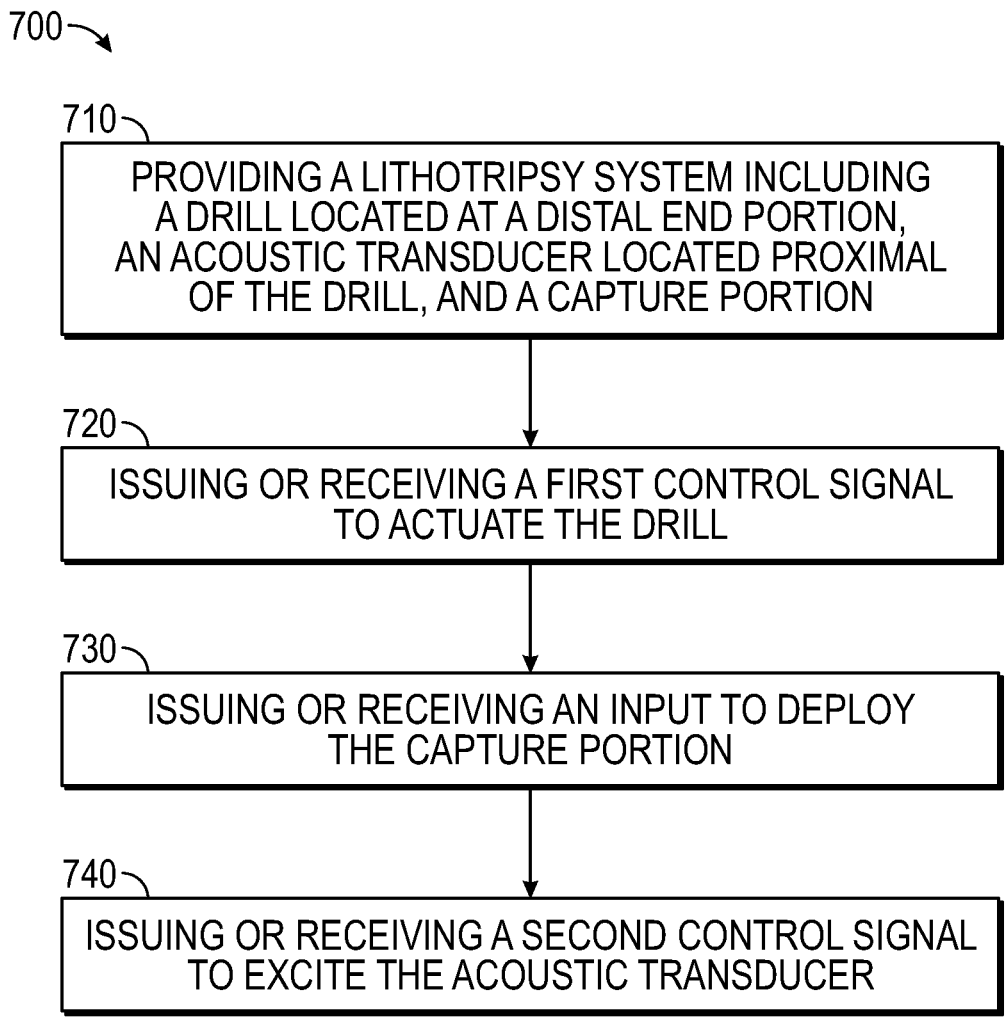
FIG. 7 illustrates a flow chart of a method of controlling a lithotripter, in accordance with at least one example.

FIG. 7 is a flow chart illustrating a method 700 to treat a mobile calculus such as a stone in a kidney, bladder, ureter or gallbladder. The method 700 can be performed using any of the lithotripsy systems 100, 200, 300, 400 and 500 of FIG. 1-3, 4A, 4B, 5A and 5B can be used with the method 700, but the method 700 can also be used with other lithotripsy systems. Likewise, the lithotripsy systems 100, 200, 300, 400 and 500 of FIGS. 1-3, 4A, 4B, 5A and 5B. can be used with other methods. The method 700 can be used separately or together with the method 600. In some examples, steps of the method 700 can be omitted or added.

Step 710 can include providing a lithotripsy system including a drill located at a distal end portion, an acoustic transducer located proximal of the drill, and a capture portion. In some examples, the drill and acoustic transducer can be coupled to a probe. In other examples the drill and the acoustic transducers can be provided on different probes, such as at the distal end of different delivery members that are delivered separately through a working channel (WC; FIG. 1).

In some examples, step 710 can include providing a delivery member having a tubular structure including an outer surface and a fluid delivery channel extending therethrough. The fluid delivery channel can be in fluid communication with a fluid port in the surface. The fluid port can be configured to deliver fluid to a stone to deteriorate or fracture a stone.

Step 720 can include issuing or receiving a first control signal to actuate the drill. In some examples the first control signal actuates a longitudinal emitter such as a longitudinal sonic transducer. In other examples, the first control signal actuates delivery of fluid to a distal fluid port located at a distal tip of the probe.

Step 730 can include issuing or receiving an input to deploy the capture portion. However, some example systems described herein do not include a capture portion.

Step 740 can include issuing or receiving a second control signal to excite the acoustic transducer.

In some examples, additional steps can include issuing or receiving a control signal to dispense fluid from the fluid opening to fracture a stone. Further, the method 700 can include issuing or receiving a control signal to actuate a suction system that causes suction to occur in a region proximate a distal end of a working channel, wherein the working channel is configured to allow delivery of the drill, the acoustic transducer and the capture portion therethrough. The method 700 can also include issuing or receiving a control signal to actuate a suction system that causes suction to occur in a region proximate a distal end of a working channel (WC; FIG. 1) of an endoscope. The working channel can be configured to allow delivery of the drill, the acoustic transducer and the capture portion therethrough.

In some non-limiting examples, the control signals can be received from any suitable source, such as the signal generator described in FIG. 1. The input can be issued by or received from an operator of the system, such as by the actuator and actuation motion described in FIGS. 2, 4A and 4B.

The benefits of the systems and methods of the present disclosure can include: improved speed of performing a lithotripsy procedure, reduced temperatures of the treatment site proximate the stone being treated, improved capture of a stone, and improved collection of fragmented stones for removal which reduces the frequency that a surgeon has to "chase down" a stone to retrieve it.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

VARIOUS NOTES AND EXAMPLES

Example 1 is a system to deliver energy to treat a mobile calculus, the system comprising: a drill configured to drill a recess into the mobile calculus or a passage through the mobile calculus; and a transducer configured to be advanced into the recess or the passage and to transmit the energy internal to the mobile calculus to fragment the mobile calculus.

In Example 2, the subject matter of Example 1 includes, wherein the transducer includes an acoustic transducer.

In Example 3, the subject matter of Examples 1-2 includes, wherein at least a portion of the drill is located at a distal end portion of a delivery member having an elongate shaft that is deliverable to a treatment site through a working channel, and wherein the transducer and the drill are coupled to the elongate shaft with the transducer located proximal of the drill.

In Example 4, the subject matter of Examples 1-3 includes, a capture portion configured to constrain movement of at least a portion of the mobile calculus relative to the capture portion.

In Example 5, the subject matter of Example 4 includes, wherein the capture portion is configured to capture at least a portion of the fragmented mobile calculus to be removed.

In Example 6, the subject matter of Examples 4-5 includes, wherein the capture portion is located at a distal end portion of a delivery member having an elongate shaft, and wherein the capture portion is configured to be advanced through the passage and to be deployed distal of the mobile calculus.

In Example 7, the subject matter of Examples 4-6 includes, wherein the capture portion includes a deformable strut configured to expand into a deployed position.

In Example 8, the subject matter of Examples 4-7 includes, wherein the capture portion includes a receiving opening configured to receive the mobile calculus.

In Example 9, the subject matter of Examples 4-8 includes, wherein the capture portion includes a receiving opening and a closure member, and wherein the capture portion is deployable from a compressed state when positioned in a working channel to a receiving state when deployed distally from the working channel, and wherein in the receiving state the capture portion is configured to receive the mobile calculus through the receiving opening, and wherein when the closure member is actuated, the receiving opening deforms to enable the capture portion to constrain the mobile calculus in a captured state.

In Example 10, the subject matter of Examples 1-9 includes, a delivery member having an elongate shaft including a tubular structure including a surface and a fluid delivery channel extending therethrough, the fluid delivery channel in fluid communication with a fluid port in the surface, wherein the fluid port is configured to provide fluid into the recess or the passage to deteriorate the mobile calculus, and wherein the drill and the transducer are coupled to the elongate shaft.

In Example 11, the subject matter of Example 10 includes, wherein the fluid port includes a plurality of fluid ports that are longitudinally spaced-apart apart along a length of the elongate shaft.

In Example 12, the subject matter of Examples 10-11 includes, wherein the fluid port includes a plurality of fluid ports that are radially spaced-apart around the elongate shaft.

In Example 13, the subject matter of Examples 1-12 includes, a delivery member having an elongate shaft including a tubular structure and a fluid delivery channel extending therethrough, wherein the drill is located at a distal end of the elongate shaft, and wherein the drill comprises a fluid port that is in fluid communication with the fluid delivery channel, the fluid port configured to supply a fluid to drill the recess or the passage in the mobile calculus.

Example 14 is a method to treat a mobile calculus in a patient, the method comprising: drilling a hole in the mobile calculus to create a recess into the mobile calculus or a passage through the mobile calculus; advancing an acoustic transducer into the recess or the passage; and exciting the acoustic transducer to transmit acoustic energy to the mobile calculus to fragment the mobile calculus.

In Example 15, the subject matter of Example 14 includes, deploying a capture portion configured to receive and constrain at least a portion of the mobile calculus.

In Example 16, the subject matter of Examples 14-15 includes, deploying a capture portion including a receiving opening; receiving the mobile calculus into the receiving opening to capture the mobile calculus; constraining movement of the mobile calculus relative to the acoustic transducer; and exciting the acoustic transducer.

In Example 17, the subject matter of Examples 14-16 includes, capturing at least portion of the fragmented mobile calculus and removing the mobile calculus from the patient.

In Example 18, the subject matter of Examples 14-17 includes, suctioning a region around at least a portion of the fragmented mobile calculus to move at least a portion of the fragmented mobile calculus into a working channel.

In Example 19, the subject matter of Examples 14-18 includes, providing fluid through a delivery member having a tubular structure including a surface and a fluid delivery channel extending therethrough, the fluid delivery channel in fluid communication with a fluid port in the surface, wherein providing the fluid causes the fluid to be dispensed from the fluid port into the recess or the passage to cause deterioration of the mobile calculus.

Example 20 is a method of controlling a lithotripter, the method comprising: providing a lithotripsy system including a drill located at a distal end portion, an acoustic transducer located proximal of the drill, and a capture portion; issuing or receiving a first control signal to actuate the drill; issuing or receiving an input to deploy the capture portion; and issuing or receiving a second control signal to excite the acoustic transducer.

In Example 21, the subject matter of Example 20 includes, wherein providing the lithotripsy system includes providing a delivery member having a tubular structure including a surface and a fluid delivery channel extending therethrough, the fluid delivery channel in fluid communication with a fluid port in the surface, and the method further comprises: issuing or receiving a control signal to dispense fluid from the fluid port.

In Example 22, the subject matter of Examples 20-21 includes, issuing or receiving a control signal to actuate a suction system that causes suction to occur in a region proximate a distal end of a working channel, wherein the working channel is configured to allow delivery of the drill, the acoustic transducer and the capture portion therethrough.

Example 23 is a system to deliver energy to treat a mobile calculus, the system comprising: a drill configured to drill a recess into the mobile calculus or a passage through the mobile calculus; and an energy emitter configured to be advanced into the recess or the passage and to transmit energy internal to the mobile calculus to fragment the mobile calculus.

In Example 24, the subject matter of Example 23 includes, wherein the energy emitter includes at least one of an acoustic transducer, an optoacoustic transducer, a laser node or a fluid jet.

In Example 25, the subject matter of Examples 23-24 includes, wherein the energy emitter emits energy in a lateral direction.

Example 26 is at least one machine-readable medium including instructions that, when executed by processing circuitry, cause the processing circuitry to perform operations to implement of any of Examples 1-25.

Example 27 is an apparatus comprising means to implement of any of Examples 1-25.

Example 28 is a system to implement of any of Examples 1-25.

Example 29 is a method to implement of any of Examples 1-25.

What is claimed is:
1. A system to deliver energy to treat a mobile calculus, the system comprising:

a drill configured to drill a recess into the mobile calculus or a passage through the mobile calculus; and a transducer configured to be advanced into the recess or the passage and to transmit the energy internal to the mobile calculus to fragment the mobile calculus wherein at least a portion of the drill is located at a distal end portion of a delivery member having an elongate shaft that is deliverable to a treatment site through a working channel, and wherein the transducer and the drill are coupled to the elongate shaft with the transducer located proximal of the drill.

2. The system of claim 1, wherein the transducer includes an acoustic transducer.

3. The system of claim 1, comprising a capture portion configured to constrain movement of at least a portion of the mobile calculus relative to the capture portion.

4. The system of claim 3, wherein the capture portion is configured to capture at least a portion of the fragmented mobile calculus to be removed.

5. The system of claim 3, wherein the capture portion is located at a distal end portion of the elongate shaft, and wherein the capture portion is configured to be advanced through the working channel and to be deployed distal of the mobile calculus.

6. The system of claim 3, wherein the capture portion includes a deformable strut configured to expand into a deployed position.

7. The system of claim 3, wherein the capture portion includes a receiving opening configured to receive the mobile calculus.

8. The system of claim 3, wherein the capture portion includes a receiving opening and a closure member, and wherein the capture portion is deployable from a compressed state when positioned in the working channel to a receiving state when deployed distally from the working channel, and wherein in the receiving state the capture portion is configured to receive the mobile calculus through the receiving opening, and wherein when the closure member is actuated, the receiving opening deforms to enable the capture portion to constrain the mobile calculus in a captured state.

9. The system of claim 1, wherein:
the delivery member having the elongate shaft includes a tubular structure including a surface and a fluid delivery channel extending therethrough, the fluid delivery channel in fluid communication with a fluid port in the surface, wherein the fluid port is configured to provide fluid into the recess or the passage to deteriorate the mobile calculus, and wherein the drill and the transducer are coupled to the elongate shaft.

10. The system of claim 9, wherein the fluid port includes a plurality of fluid ports that are longitudinally spaced apart along a length of the elongate shaft.

11. The system of claim 9, wherein the fluid port includes a plurality of fluid ports that are radially spaced apart around the elongate shaft.

12. The system of claim 1, further comprising:
a delivery member having an elongate shaft including a tubular structure and a fluid delivery channel extending therethrough, wherein the drill is located at a distal end of the elongate shaft, and wherein the drill comprises a fluid port that is in fluid communication with the fluid delivery channel, the fluid port configured to supply a fluid to drill the recess or the passage in the mobile calculus.

13. A method to treat a mobile calculus in a patient, the method comprising:
drilling a hole in the mobile calculus with a drill to create a recess into the mobile calculus or a passage through the mobile calculus, the drill coupled to a distal end portion of an elongate shaft that is deliverable to a treatment site through a working channel;
advancing an acoustic transducer into the recess or the passage, the acoustic transducer being coupled to the elongate shaft proximal of the drill; and
exciting the acoustic transducer to transmit acoustic energy to the mobile calculus to fragment the mobile calculus.

14. The method of claim 13, further comprising:
deploying a capture portion configured to receive and constrain at least a portion of the mobile calculus.

15. The method of claim 13, further comprising:
deploying a capture portion including a receiving opening;
receiving the mobile calculus into the receiving opening to capture the mobile calculus;
constraining movement of the mobile calculus relative to the acoustic transducer; and
exciting the acoustic transducer.

16. The method of claim 13, further comprising:
capturing at least portion of the fragmented mobile calculus and removing the mobile calculus from the patient.

17. The method of claim 13, further comprising:
suctioning a region around at least a portion of the fragmented mobile calculus to move at least a portion of the fragmented mobile calculus into a working channel.

18. The method of claim 13, further comprising:
providing fluid through a delivery member having a tubular structure including a surface and a fluid delivery channel extending therethrough, the fluid delivery channel in fluid communication with a fluid port in the surface, wherein providing the fluid causes the fluid to be dispensed from the fluid port into the recess or the passage to cause deterioration of the mobile calculus.

19. A system to deliver energy to treat a mobile calculus, the system comprising:
a drill configured to drill a recess into the mobile calculus or a passage through the mobile calculus; and
an energy emitter configured to be advanced into the recess or the passage and to transmit energy internal to the mobile calculus to fragment the mobile calculus
wherein at least a portion of the drill is located at a distal end portion of a delivery member having an elongate shaft that is deliverable to a treatment site through a working channel, and wherein the energy emitter and the drill are coupled to the elongate shaft with the energy emitter located proximal of the drill.

20. The system of claim 19, wherein the energy emitter includes at least one of an acoustic transducer, an optoacoustic transducer, a laser node or a fluid jet.

21. The system of claim 19, wherein the energy emitter emits energy in a lateral direction.

* * * * *